US011835531B2

(12) United States Patent
Struck et al.

(10) Patent No.: US 11,835,531 B2
(45) Date of Patent: Dec. 5, 2023

(54) PROCALCITONIN FOR THE PROGNOSIS OF ADVERSE EVENTS

(71) Applicant: B.R.A.H.M.S GmbH, Hennigsdorf (DE)

(72) Inventors: Joachim Struck, Berlin (DE); S. J. L. Bakker, Groningen (NL)

(73) Assignee: B.R.A.H.M.S GmbH, Hennigsdorf (DE)

( * ) Notice: Subject to any disclaimer, the term of this patent is extended or adjusted under 35 U.S.C. 154(b) by 127 days.

(21) Appl. No.: 16/377,465

(22) Filed: Apr. 8, 2019

(65) Prior Publication Data

US 2019/0227081 A1    Jul. 25, 2019

Related U.S. Application Data

(63) Continuation of application No. 13/392,109, filed as application No. PCT/EP2010/062597 on Aug. 27, 2010, now abandoned.

(30) Foreign Application Priority Data

Aug. 28, 2009   (EP) .................................... 09011073

(51) Int. Cl.
*G01N 33/543* (2006.01)
*G01N 33/68* (2006.01)

(52) U.S. Cl.
CPC ... *G01N 33/6893* (2013.01); *G01N 2333/585* (2013.01); *G01N 2800/042* (2013.01); *G01N 2800/2871* (2013.01); *G01N 2800/324* (2013.01); *G01N 2800/50* (2013.01)

(58) Field of Classification Search
None
See application file for complete search history.

(56) References Cited

U.S. PATENT DOCUMENTS

| 5,993,811 | A | * | 11/1999 | Becker ................... A61P 33/00 424/139.1 |
| 6,596,476 | B1 | * | 7/2003 | Lesniewski .......... C07K 14/005 435/5 |
| 8,465,941 | B2 | | 6/2013 | Bergmann et al. |
| 9,513,301 | B2 | | 12/2016 | Bergmann et al. |
| 9,664,689 | B2 | | 5/2017 | Bergmann et al. |
| 2004/0082031 | A1 | | 4/2004 | Hui et al. |
| 2004/0241744 | A1 | * | 12/2004 | Kohno ................... G01N 33/92 435/7.1 |
| 2005/0244904 | A1 | * | 11/2005 | Ng ..................... G01N 33/6893 435/7.92 |
| 2012/0003751 | A1 | | 1/2012 | Bergmann et al. |

FOREIGN PATENT DOCUMENTS

| CA | 2511501 | A1 | 7/2004 |
| CN | 1509332 | A | 6/2004 |
| CN | 1751128 | A | 3/2006 |
| CN | 101246163 | A | 8/2008 |
| JP | 2006161433 | A | 6/2006 |
| JP | 2007327921 | A | 12/2007 |
| JP | 2009103721 | A | 5/2009 |
| JP | 2010536012 | A | 11/2010 |
| JP | 2012505388 | A | 3/2012 |
| WO | 08040328 | A2 | 4/2008 |
| WO | 08104321 | A1 | 9/2008 |

OTHER PUBLICATIONS

Harlow, E. and Lane, D., Antibodies: A Laboratory Manual (1988) Cold Spring Harbor Laboratory Press, Cold Spring Harbor, NY, pp. 23-26 (Year: 1988).*
Colman et al. Research in Immunology, 1994; 145(1): 33-36 (Year: 1994).*
Lederman et al. "A single amino acid substitution in a common African allele of the CD4 molecule ablates binding of the monoclonal antibody, OKT4" Mol Immunol. Nov. 1991;28(11):1171-81 (Year: 1991).*
Sfia et al., High Procalcitonin Levels in Patients with Severe Drug Reactions, Arch Dermatol., vol. 143, No. 12, p. 1591, 2007. (Year: 2007).*
Qedra, N. et al., "Procalcitonin and modified SOFA score: The best predictors of mortality after heart and lung transplantation," Journal of Heat and Lung Transplantation, Feb. 1, 2004, vol. 23, No. 2S, p. S117, Mosby-Year Book, Inc., St. Louis, MO; Cited in the International Search Report, dated Oct. 15, 2010, issued in corresponding PCT/EP2010/062597.
Fazakas, J. et al., "Analysis of systemic and regional procalcitonin serum levels during liver transplantation," Transplant International, Jul. 1, 2003, vol. 16, No. 7, pp. 465-470, Springer International, Berlin, Germany; Cited in the International Search Report, dated Oct. 15, 2010, issued in corresponding PCT/EP2010/062597.
Prat, C. et al., "Serum concentrations of procalcitonin after cardiac surgery," Journal of Cardiac Surgery Nov.-Dec. 2008, Nov. 2008, vol. 23, No. 6, pp. 627-632, Wiley Periodicals, Inc.; Cited in the International Search Report, dated Oct. 15, 2010, issued in corresponding PCT/EP2010/062597.
Barassi, A., et al., "Biological Variation of Procalcitonin in Healthy Individuals," Clinical Chemistry, Oct. 2004, vol. 50, No. 10, p. 1878; Cited in the International Search Report, dated Oct. 15, 2010, issued in corresponding PCT/EP2010/062597.
Assumma, M., et al., "Serum Procalcitonin Concentrations in Term Delivering Mothers and Their Healthy Offspring: A Longitudinal Study," Clinical Chemistry, Oct. 2000, vol. 46, No. 10, pp. 1583-1587; Cited in the International Search Report, dated Oct. 15, 2010, issued in corresponding PCT/EP2010/062597.

(Continued)

*Primary Examiner* — Gary Counts
(74) *Attorney, Agent, or Firm* — MILLEN, WHITE, ZELANO & BRANIGAN, PC; Ryan Pool

(57) ABSTRACT

An in vitro method for the prognosis of an adverse event in asymptomatic subjects comprising the determination of the level of Procalcitonin (PCT) or a fragment thereof or a precursor or fragment thereof having at least 12 amino acid residues in a sample of a bodily fluid from the subject and the correlation of the determined level to a potential risk of sustaining an adverse event.

4 Claims, No Drawings

Specification includes a Sequence Listing.

(56) References Cited

OTHER PUBLICATIONS

International Search Report, dated Oct. 15, 2010, issued in corresponding PCT/EP2010/062597.
Written Opinion, dated Oct. 15, 2010, issued in corresponding PCT/EP2010/062597.
Morgenthaler et al., Sensitive Immunoluminometric Assay for the Detection of Procalcitonin, Clinical Chemistry 48, No. 6, 2002, pp. 788-790.
Nils et al., Sensitivie Immunoluminometiric Assay for the Detection of Procalcitonin, Clinical Chemistry 48, No. 5, 2002, pp. 788-790.
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.

\* cited by examiner

PROCALCITONIN FOR THE PROGNOSIS OF ADVERSE EVENTS

REFERENCE TO SEQUENCE LISTING

This application contains a Sequence Listing submitted in electronic and print form. The electronic and print form of the Sequence Listing are identical to each other pursuant to 37 CFR § 1.52(e)(4), contains the following file: "BOEHMERP0116SQL.txt", having a size in bytes of 1.26 KB, recorded on Nov. 1, 2011. The information contained in the sequence listing is hereby incorporated by reference in its entirety pursuant to 37 CFR § 1.52(e)(5).

FIELD OF THE INVENTION

The present invention is in the field of clinical diagnostics. Particularly the present invention relates to the determination of the level of Procalcitonin (PCT) in a sample derived from a bodily fluid of a subject.

BACKGROUND OF THE INVENTION

Procalcitonin (PCT) is known as a biomarker, that reflects the presence and severity of local and systemic bacterial infections, i.e. sepsis (Assicot et al., Lancet 1993; 341:515-8; Muller et al., Crit Care Med 2000; 28:977-83; Harbarth et al., Am J Respir Crit Care Med 2001; 164:396-402; Becker et al., Crit Care Med 2008; 36:941-52; Becker et al., J Clin Endocrinol Metab 2004; 89:1512-25; Nobre et al., Am J Respir Crit Care Med 2008; 177:498-505; Christ-Crain et al., Lancet 2004; 363:600-7; Stolz et al., Chest 2007; 131:9-19; Christ-Crain et al., Am J Respir Crit Care Med 2006; 174:84-93; Briel et al., Arch Intern Med 2008; 168:2000-7; discussion 7-8).

During bacterial infections, plasma PCT concentrations are typically above 0.25 ng/mL. More recently, using highly sensitive assay technologies, it has been found that in several non-infectious diseases PCT concentrations can be elevated to the upper concentration range of the normal range or above, but below the concentrations which have been known to be associated with bacterial infections requiring antibacterial treatment. Moreover, it has been found that these PCT concentrations are associated with an unfavorable prognosis for these patients.

These diseases include coronary artery disease and acute coronary syndromes. There are only two publications which describe the quantitative PCT concentrations in healthy individuals (Morgenthaler et al., Clin Chem 2002, 48:788-790; Morgenthaler et al., Clin Lab 2002, 48:263-270). However, it is unknown whether relatively elevated PCT concentrations in healthy individuals can be associated with the occurrence of potential future adverse events. The possibility of predicting future adverse events for individuals which are apparently healthy at presentation is important, since early recognition of risk is a prerequisite for initiating measures helping to prevent the development of adverse events.

It has thus been an object of the present invention to establish a link between PCT levels in the apparently healthy (asymptomatic) population with the prognosis of adverse events.

SUMMARY OF THE INVENTION

The present invention is based on the surprising finding that the PCT levels in samples from asymptomatic subjects, who have later suffered from an adverse event, are increased relative to PCT levels in samples from asymptomatic subjects who will not suffer from an adverse event in a statistically relevant manner.

The present invention relates to an in vitro method for the prognosis of an asymptomatic subject to experience an adverse event. The method comprises: First, the level of procalcitonin (PCT) or fragments thereof in a sample from the subject is determined. Secondly, the level of procalcitonin or fragments thereof is correlated to a risk of the subject to suffer from an adverse event.

DETAILED DESCRIPTION OF THE INVENTION

The present invention relates to a method for determining the risk of an apparently healthy subject for suffering from an adverse event or for determining the presence of absence of an increased risk of an apparently healthy subject for suffering from an adverse event in the future. Preferably, the risk of the occurrence of adverse events during a time period of about 6 months to 10 years can be predicted. The method comprises the following steps: First, a sample is provided from the subject. Secondly, the level of procalcitonin (PCT) or of a fragment thereof is determined in the sample. Thirdly, the risk of the subject for getting an adverse event based is determined based on the PCT level or it is determined whether the subject has an increased risk for suffering from an adverse event based on said PCT level.

The term "risk" refers to a probability for a subject to suffer in the future from a certain adverse event.

"Subject" as used herein refers to a living human or non-human organism. In a preferred embodiment, the subject is a human being. Furthermore, it is preferred that the subject is free of (symptomatic) bacterial infections at the time the sample from the subject is obtained from the subject. This ensures that the PCT levels are not increased above the normal range in the subject. Therefore, the subject is preferably tested for bacterial infections prior to performing the method of the invention.

The "apparently healthy" subject is preferably also free of any non-infectious diseases, i.e. the subject does not show any symptoms that would allow a diagnosis of a non-infectious disease. The term "non-infectious disease" refers to diseases such as hypertension, orthopaedic diseases such as osteoporosis, and neurodegenerative diseases such as Alzheimer's disease. It is known that the PCT concentration is enhanced in neonates because of the post-natal trauma. Therefore, neonates are excluded from the claims. Neonates according to the definitions of the present inventions have preferably an age between 1 day to 10 days, more preferably one day to 3 days. It is also known that PCT concentrations are enhanced in patients after surgery, e.g. after organ transplantation as heart transplantation, lung transplantation, liver transplantation, kidney transplantation, cardiac surgery. Thus, patients after surgery, e.g. after organ transplantation as heart transplantation, lung transplantation, liver transplantation, kidney transplantation, cardiac surgery are excluded from the group of healthy persons if the surgery has been conducted within the last seven days, preferably post-surgery patients are excluded if the surgery has been conducted within the last fourteen days. In another embodiment post-surgery patients are excluded which underwent surgery within the last two months. Preferentially, post-trauma patients and persons are excluded which experienced said trauma within the last 14 days, preferably 7 days.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus in a preferred embodiment of the invention, the sample is selected from the group consisting of a blood sample, a serum sample, a plasma sample, a cerebrospinal fluid sample, a saliva sample and an urine sample or an extract of any of the aforementioned samples. Preferably, the sample is a blood sample, most preferably a serum sample or a plasma sample.

In the present invention, the term "prognosis" denotes a prediction of how a subject's (e.g. a patient's) medical condition will progress. This may include an estimation of the chance of an adverse event to occur for said subject.

An "adverse event" or adverse outcome is defined as an event or outcome compromising the health of an individual. Said adverse event is not restricted to, but may be selected from the group comprising a cardiac event, a cardiovascular event, a cerebrovascular event, a cancer, diabetes, and death due to all causes. An adverse event includes infections, serious infections and sepsis-like systemic infections and sepsis. An adverse is not an event caused by an acute exogene induced adverse event and/or exogene induced trauma. Exogene induced trauma include those which may be induced by accidents, e.g. car accidents. Exogene induces trauma are therefore excluded from the group of adverse events.

A cardiac event was defined as the sum of any of the following events: acute myocardial infarction (ICD-code 410), acute and subacute ischemic heart disease (ICD-code 411), and the following procedures: coronary artery bypass grafting or percutaneous transluminal coronary angioplasty.

A cerebrovascular event was defined as the sum of any of the following events: occlusion or stenosis of the precerebral (ICD-code 433) or cerebral arteries (ICD-code 434).

Cardiovascular mortality was defined as death due to a cardiac or cerebrovascular event. Total cardiovascular events were defined as the sum of cardiac events, cerebrovascular events and cardiovascular mortality.

As mentioned herein, in the context of proteins or peptides, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

Procalcitonin in the context of the present invention preferably relates to a peptide spanning amino acid residues 1-116, 2-116, or 3-116 or fragments thereof. Thus, the length of procalcitonin fragments should be at least 12 or 15 amino acids, preferably more than 50 amino acids, more preferably more than 100 or 110 amino acids.

PCT may comprise posttranslational modifications such as glycosylation, liposidation or derivatisation. PCT itself is a precursor of calcitonin and katacalcin. The amino acid sequence of PCT 1-116 is given in SEQ ID NO. 1.

The term "level" in the context of the present invention relates to the concentration (preferably expressed as weight/volume; w/v) of PCT (or a fragment/precursor) in a sample taken from a subject.

Determining (or measuring or detecting) the level of PCT or a fragment or a precursor or fragment thereof herein is performed using a detection method and/or a diagnostic assay as explained below.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of Lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The determination of the PCT level is preferably performed using a (polyclonal or preferably monoclonal) antibody, particularly an antibody that specifically binds to the katacalcin moiety or the calcitonin moiety of PCT.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134, incorporated herein by reference).

In a particularly preferred embodiment, the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5-or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY® borondipyrromethene fluorescent dyes, such as BODIPY® borondipyrromethene fluorescent dye TMR, Oregon Green, Coumarins such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrin dyes, Polymethin dyes, and the like. In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridinium esters.

In the method of the invention, several ways of determining an increased risk of an apparently healthy subject for suffering from an adverse event can be applied. The method may involve comparing the level of PCT in the subject with a predetermined value for PCT in a comparable population. This can be a single cut-off value, e.g. a median or mean or the 75$^{th}$, 90$^{th}$, 95$^{th}$ or 99$^{th}$ percentile of a population. Alternatively, a range can be used, e.g. where the tested population is divided equally or unequally into groups (e.g. a low, medium or high risk group) or into quartiles, the lowest quartile being individuals with the lowest risk and the highest quartile being individuals with the highest risk.

The predetermined value can vary among particular populations selected, depending on certain factors, such as gender, age, genetics, habits, ethnicity or alike.

Preferably, the risk determination is performed by using of the following alternatives:

comparing the determined PCT or PCT fragment level with the median of the level of PCT or fragments thereof in an ensemble of predetermined samples from a population of apparently healthy subjects, or comparing the determined PCT or PCT fragment level with a quantile of the level of PCT or fragments thereof in an ensemble of predetermined samples from a population of apparently healthy subjects, or performing calculations based on Cox Proportional Hazards analysis or on risk index calculations such as the Net Reclassification Index (NRI) or the Integrated Discrimination Index (IDI).

In other embodiments, odds ratio, or hazard ratio is used as a measure of a test's ability to predict risk or diagnose a disease.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 1.5 or more or about 0.75 or less, more preferably at least about 2 or more or about 0.5 or less, still more preferably at least about 3 or more or about 0.33 or less, even more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

As can be seen e.g. in table 6, the inventors were able to establish cut-off values for PCT levels that are indicative for the subject to suffer from a certain adverse event in the future. Generally, a subject can be determined of being at risk for suffering from an adverse event when the PCT level in a serum sample is at least 0.015 ng/ml serum, preferably at least 0.02 ng/ml.

Specifically, the subject is determined of being at an increased risk for suffering from a cardiac event or a cardiovascular event when said PCT level in a serum sample is at least 0.0155 ng/ml serum. The subject is determined of being at an increased risk for suffering from a cerebrovascular event or from dying due to cardiovascular cause when the determined PCT level in a serum sample is at least 0.0215 ng/ml. The subject is determined of being at an increased risk for dying from cancer when the PCT level in a serum sample is at least 0.0155 ng/ml. The subject is determined of being at an increased risk for dying from cancer when the PCT level in a serum sample is at least 0.0155 ng/ml. The subject is determined of being at an increased risk for dying when said PCT level in a serum sample is at least 0.0205 ng/ml, and is determined of being at risk for suffering from diabetes when the PCT level in a serum sample is at least 0.0185 ng/ml.

It is preferred that in the method of the invention at least one further parameter is determined and used to determine the risk or increased risk of suffering from an adverse event.

Such a further parameter can be a clinical parameter, a laboratory (i.e. biochemical) parameter and/or a genetic parameter.

Suitable threshold levels for the stratification of subjects into different groups (categories) can e.g. be done by grouping a reference population of patients according to their level of PCT into certain quantiles, e.g. tertiles, quartiles, quintiles or even according to suitable percentiles. For each of the quantiles or groups above and below certain percentiles, hazard ratios can be calculated comparing the risk for an e.g. adverse outcome, i.e. an "unfavourable effect" or increased risk, e.g. in terms of survival rate. In such a scenario, a hazard ratio (HR) above 1 indicates a higher risk for an adverse outcome for the patients. A HR below 1 indicates a lower risk. A HR around 1 (e.g. +/−0.1) indicates no elevated risk for the particular group of patients. By comparison of the HR between certain quantiles of patients with each other and with the HR of the overall population of patients, it is possible to identify those quantiles of patients who have an elevated level and enhanced risk and thereby stratify subjects according to the present invention.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from bacterial infections). For any particular marker, a distribution of marker levels for subjects with and without a disease will likely overlap. Under such conditions, a test does not absolutely distinguish normal from disease or patients with enhanced risk from those which have no enhanced risk with 100% accuracy, and the area of overlap indicates where the test cannot distinguish normal from disease; enhanced risk from those who haven't. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (Hanley et al. 1982. *Radiology* 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

The odds ratio is a measure of effect size, describing the strength of association or non-independence between two binary data values (e.g. the ratio of the odds of an event occurring in test negative group to the odds of it occurring in the test positive group).

The positive predictive value (PPV), or precision rate, is the proportion of patients with positive test results who are correctly diagnosed and/or predicted. It reflects the probability that a positive test reflects the underlying condition being tested for. The negative predictive value (NPV) is the proportion of patients with negative test results who are correctly diagnosed and/or predicted. The total accuracy is the percentage of all patients classified correctly with the test.

Specifically, the at least one clinical parameter can be selected from the group consisting of gender (i.e. male or female), age, systolic blood pressure, systolic blood pressure, diastolic blood pressure, body mass index, waist circumference, waist-hip ratio, and smoking habit.

In particular, because PCT levels are significantly different between male and female (see e.g. Table 2), the gender of the subject is a parameter that needs to be considered when performing the method of the invention.

The at least one laboratory parameter can be selected from the group consisting of fasting blood or plasma glucose concentration, triglycerides, cholesterol concentration, and HDL cholesterol concentration and subfractions thereof, LDL cholesterol concentration and subfractions thereof, cystatin C, insulin, CRP, natriuretic peptides of the A- and B-type as well as their precursors and fragments thereof including ANP, proANP, NT-proANP, MR-proANP, BNP, proBNP, NT-proBNP, GDF15, ST2, procalcitonin and fragments thereof, pro-adrenomedullin and fragments thereof including ADM, PAMP, MR-proADM, CT-proADM, pro-Endothelin-1 and fragments thereof including CT-proET-1, NT-proET-1, big-Endothelin-1, and Endothelin-1.

The at least one genetic parameter is preferably selected from the group consisting of single nucleotide polymorphisms (SNPs), and mutations.

The method of the invention provides information as to a possible increased risk of a subject for suffering from an adverse event, as described above and herein. Based on this information, preventive measures can be taken in order to avoid the adverse event from occurring in the subject. The preventive measures may be, e.g. taking appropriate medicine, following dietary restrictions, exercising, obtaining medical supervision and others.

In a further aspect, the invention refers to the use of a method as described above and herein for determining an increased risk of an apparently healthy subject for suffering from an adverse event.

Furthermore, the invention pertains to the use of a kit comprising one or more antibodies directed against PCT or a fragment thereof or a precursor or fragment thereof for the prognosis of an asymptomatic subject to experience an adverse event, i.e. for performing a method as described herein.

Examples

Study Population and Design

The study population was obtained from the Prevention of Renal and Vascular Endstage Disease (PREVEND) study. The PREVEND study was designed to investigate prospectively the natural course of albuminuria and its relation to renal and cardiovascular disease in a large cohort drawn from the general population (age ranged between 28 and 75 years) of the city of Groningen, the Netherlands. Details of the study design, recruitment, and procedures have been published elsewhere (Hillege et al., Circulation 2002, 106: 1777-1782; Hillege et al., J Intern Med 2001, 249:519-526; Mahmoodi et al., JAMA 2009, 301:1790-1797). The PREVEND study was approved by the local medical ethics committee, University Medical Center Groningen, and conformed to the principles outlined in the Declaration of Helsinki. All participants gave written informed consent.

Measurements

The participants underwent two outpatient visits to assess demographic, anthropometric, and cardiovascular risk factors. They completed a questionnaire on demographics, Cardiovascular disease (CVD) history, smoking habits, family history of CVD, alcohol consumption and medication use prior to their first visit. The participants were investigated for total cholesterol level, high-density lipoprotein (HDL) cholesterol, triglycerides, measured blood pressure, serum creatinine and diabetes mellitus. Diabetes was defined according to the guidelines of the American Diabetes Association as a fasting plasma glucose≥7.0 mmol/l or the use of antidiabetic medication. Furthermore, information on medication use was substantiated with use of pharmacy-dispensing data from all community pharmacies in the city of Groningen.

At baseline, CVD was defined by history of prior major cardiovascular events (i.e., myocardial infarction, cerebrovascular accident), history of coronary angioplasty and/or bypass surgery, ankle/brachial index less than 0.9, or presence of QS pattern based on the Minnesota classification (i.e., 1.1 and 1.2 codes). Individuals with CVD at presentation were excluded from the study. Individuals with diabetes at presentation were excluded from the study. Individuals having any cancer at presentation were excluded from the study. Individuals with a serum creatinine>132 μmol/L were considered as having renal dysfunction and were excluded from the study. The total number of individuals eligible for the study was n=5313. Thus, the population investigated in this study was a representative population of apparently non-diseased people, representative for the general healthy population.

On the time point of inclusion, a blood sample was taken from each individual for making laboratory measurements (see below).

The investigated population was followed for ten years, and the occurrence of various endpoints was recorded: The endpoints of the study were incident cardiac events, incident cerebrovascular events, cardiovascular mortality, total cardiovascular events, incident diabetes, cancer mortality and total mortality. A cardiac event was defined as the sum of any of the following events: acute myocardial infarction (ICD-code 410), acute and subacute ischemic heart disease (411), and the following procedures: coronary artery bypass grafting or percutaneous transluminal coronary angioplasty. A cerebrovascular event was defined as the sum of any of the following events:

occlusion or stenosis of the precerebral (433) or cerebral arteries (434). Cardiovascular mortality was defined as death due to a cardiac or cerebrovascular event. Total cardiovascular events were defined as the sum of cardiac events, cerebrovascular events and cardiovascular mortality. Diabetes was defined according to the guidelines of the American Diabetes Association as a fasting plasma glucose≥7.0 mmol/l or the use of antidiabetic medication. Cancer mortality was defined as death due to cancer. Total mortality was defined as death of any cause.

Information (on hospitalization) for cardiovascular morbidity was obtained from PRISMANT, the Dutch national registry of hospital discharge diagnoses. Data were coded according to the International Classification of Diseases, 9th revision and the classification of interventions. In case a person had moved to an unknown destination, the date on which the person was removed from the municipal registry was used as censor date. Data on mortality were received from the municipal register, and cause of death was obtained by linking the number of the death certificate to the primary cause of death as coded by the Dutch Central Bureau of Statistics.

Laboratory Assay

At baseline, blood samples were drawn after an overnight fast. Blood samples were drawn into chill tube containing EDTA. The samples were immediately centrifuged at 1500 g and 4° C. for 10 min, and the supernatants stored in aliquots at −80° C. for further use. PCT was measured as follows: A commercially available ultrasensitive sandwich assay for PCT was used (BRAHMS PCT LIA sensitive) (Morgenthaler et al. Clin Chem 2002; 48:788-90), which uses one antibody directed against the katacalcin moiety of PCT as solid phase, and one antibody directed against the calcitonin moiety of PCT as labeled antibody (BRAHMS AG, Hennigsdorf, Germany). Recombinant PCT in various concentrations is used as calibrator. A sample volume of 100 μl was used.

Statistical Analyses

Baseline descriptive statistics of the continuous variables were reported as mean±standard deviation (SD) and as median with 25th and 75th percentiles, whenever the distribution of data was skewed. The categorical variables were presented as numbers and percentages. A $\chi 2$ test was used to test the differences between groups for the categorical variables. The continuous data were compared by using Student's t test or a Mann-Whitney rank test if the variable was not normally distributed according to Kolmogorov-Smirnov test. To test the prediction value of PCT for incidence events, we fitted separately Cox proportional hazard models with the development of the various events, which had been recorded, as the dependent variables. Because of a skewed distribution, logarithmic transformation (log 2) of PCT was applied in Cox regression analysis to compute hazard ratios (HR) and 95% confidence intervals (CIs) per doubling of PCT levels. P values of 0.05 or less from two-sided tests were considered statistically significant. Additionally, hazard ratios were calculated for the second through the fifth PCT quintile in comparison to the first PCT quintile. All the statistical analyses were carried out via Statistical Package for Social Sciences version 16 (SPSS Inc, Chicago, Illinois, USA) and S-PLUS software (Insightful Corp., Seattle, Washington, USA).

Results

The baseline characteristics of the study population are summarized in Table 1.

Table 2 shows the baseline PCT levels (all) and baseline PCT levels (≤0.1 ng/ml) stratified by gender.

Analyses were performed with samples containing PCT levels≤0.1 ng/ml and with samples containing PCT levels that were also higher than 0.1 ng/ml. It was found that the prognostic value of PCT was essentially the same for both of these sample.

PCT levels were significantly different between male and female (Table 2) for the whole study group (P<0.001) as well as for subjects with PCT values≤0.1 ng/ml (P<0.001).

Tables 3 and 4 show Hazard ratios, which describe the increase of risk for developing an event, as indicated, per doubling of the PCT concentration. For instance, a Hazard ratio of 2.23 for cardiovascular mortality means that an individual with a PCT concentration of, say, 0.030 ng/mL has a 2.23-fold higher risk of dying from cardiovascular complications than an individual having a PCT concentration of 0.015 ng/mL.

Table 3 shows Hazard Ratios (95% CI) for the prediction of cardiovascular events as well as cancer, cardiovascular and total mortality by PCT levels (all and ≤0.1 ng/ml, respectively) in the whole study group.

Table 4 shows Hazard Ratios (95% CI) for the prediction of cardiovascular events as well as cancer, cardiovascular and total mortality by PCT levels (all and ≤0.1 ng/ml, respectively) stratified by gender Table 5 shows Hazard Ratios (95% CI) for the prediction of development of Type 2 Diabetes in the asymptomatic population by PCT levels (all and ≤0.1 ng/ml).

Table 6 shows cut-off values and AUC ROC. From the entire investigated population PCT values>0.1 ng/mL were excluded from this analysis. For each type of event, the Area under the receiver operator characteristics curve (AUC ROC) was calculated. Optimal cut-off values were defined as the highest mathematical product of sensitivity and specificity, which could be reached for each type of event, when testing all possible cut-off values. For the person skilled in the art it is clear that other cut-off values might be considered "optimal" depending on whether sensitivity, specificity, positive predictive value or negative predictive value are important in the particular application.

Table 7 shows the adverse events according to PCT quintiles. From the entire investigated population PCT values>0.1 ng/mL were excluded from this analysis. The population was separated in PCT concentration quintiles. For the various types of events the number of cases and proportion per quintile (in percent) are shown. The Hazard ratio for development of each type of event was calculated for quintiles Q2 through Q5 by comparison with quintile Q1. The analysis for the event type diabetes is shown separately from the other events, because the number of persons, which could be followed for this event type was smaller than for the other event types. The numbers of individuals per quintile are not perfectly even, because of a high frequency of individual values at those PCT concentrations separating the quintiles, which had to be attributed to either the upper or lower quintile at this concentration.

Taken together, the results show that elevated PCT levels in asymptomatic subjects are of prognostic value for predicting whether the subject is at risk for suffering from an adverse event in the future.

Tables

TABLE 1

| | |
|---|---|
| No. of participants | 5313 |
| Age- yr | 47.3 ± 12 |
| Men- no. (%) | 2375 (44.7) |
| Body mass index- kg/m$^2$ | 25.8 ± 4.1 |
| Waist circumference- cm | 86.9 ± 12.7 |
| Systolic blood pressure- mmHg | 122.1 ± 18.2 |
| Diastolic blood pressure- mmHg | 70.8 ± 9.4 |
| Cholesterol- mmol/l | 5.6 ± 1.1 |
| HDL cholesterol- mmol/l | 1.3 ± 0.4 |

TABLE 2

| PCT levels (all) at baseline in ng/ml (n = 5313) | | |
|---|---|---|
| Men (n = 2353) | Women (n = 2960) | P value* |
| 0.018 (0.015-0.022) | 0.014 (0.012-0.017) | <0.0001 |
| PCT levels (≤0.1 ng/ml) at baseline in ng/ml (n = 5292) | | |
| Men (n = 2337) | Women (n = 2955) | P value* |
| 0.018 (0.015-0.022) | 0.014 (0.012-0.017) | <0.0001 |

*Calculated using Mann-Whitney U test

TABLE 3

| PCT (all) at baseline (n = 5313) | | | | | |
|---|---|---|---|---|---|
| Cardiac events (n = 98) | Cerebrovascular events (n = 61) | Cardiovascular mortality (n = 30) | Total Cardiovascular events (n = 172) | Cancer mortality (n = 91) | Total mortality (n = 148) |
| 1.53 (1.26-1.87) | 1.50 (1.15-1.96) | 1.52 (1.04-2.20) | 1.52 (1.31-1.77) | 1.53 (1.24-1.89) | 1.55 (1.32-1.81) |
| PCT (≤0.1 ng/ml) at baseline (n = 5292) | | | | | |
| Cardiac events (n = 98) | Cerebrovascular events (n = 61) | Cardiovascular mortality (n = 30) | Total Cardiovascular events (n = 172) | Cancer mortality (n = 89) | Total mortality (n = 146) |
| 2.33 (1.65-3.30) | 2.18 (1.40-3.40) | 2.23 (1.18-4.18) | 2.78 (1.75-2.96) | 1.79 (1.20-2.65) | 2.07 (1.55-2.78) |

TABLE 4

| PCT (all) in men at baseline (n = 2353) | | | | | |
|---|---|---|---|---|---|
| Cardiac events (n = 46) | Cerebrovascular events (n = 30) | Cardiovascular mortality (n = 17) | Total Cardiovascular events (n = 85) | Cancer mortality (n = 41) | Total mortality (n = 73) |
| 1.51 (1.01-2.26) | 1.41 (0.82-2.42) | 0.91 (0.33-2.46) | 1.40 (1.02-1.93) | 1.95 (1.44-2.66) | 1.75 (1.34-2.29) |

TABLE 4-continued

| PCT (all) in women at baseline (n = 2960) | | | | | |
|---|---|---|---|---|---|
| Cardiac events (n = 52) | Cerebrovascular events (n = 31) | Cardiovascular mortality (n = 13) | Total Cardiovascular events (n = 87) | Cancer mortality (n = 50) | Total mortality (n = 75) |
| 1.55 (1.23-1.94) | 1.53 (1.13-2.09) | 1.67 (1.17-2.37) | 1.56 (1.31-1.85) | 1.28 (0.84-1.93) | 1.43 (1.12-1.83) |

| PCT (≤0.1 ng/ml) in men at baseline (n = 2337) | | | | | |
|---|---|---|---|---|---|
| Cardiac events (n = 46) | Cerebrovascular events (n = 30) | Cardiovascular mortality (n = 17) | Total Cardiovascular events (n = 85) | Cancer mortality (n = 40) | Total mortality (n = 72) |
| 2.04 (1.18-3.50) | 1.80 (0.90-3.60) | 1.20 (1.12-1.29) | 1.79 (1.18-2.71) | 2.29 (1.31-4.01) | 2.08 (1.35-3.19) |

| PCT (≤0.1 ng/ml) in women at baseline (n = 2950) | | | | | |
|---|---|---|---|---|---|
| Cardiac events (n = 52) | Cerebrovascular events (n = 31) | Cardiovascular mortality (n = 13) | Total Cardiovascular events (n = 87) | Cancer mortality (n = 49) | Total mortality (n = 74) |
| 2.93 (1.81-4.72) | 2.67 (1.44-4.97) | 1.14 (1.07-1.21) | 2.98 (2.06-4.29) | 1.54 (0.83-2.85) | 2.12 (1.36-3.30) |

TABLE 5

| PCT (all) at baseline | | |
|---|---|---|
| All participants (123/4206) | Men (62/1870) | Women (61/2336) |
| 1.78 (1.44-2.20) | 1.61 (1.13-2.30) | 2.18 (1.48-3.21) |

| PCT (≤0.1 ng/ml) at baseline | | |
|---|---|---|
| All participants (121/4193) | Men (60/1859) | Women (61/2334) |
| 2.11 (1.51-2.95) | 1.43 (0.84-2.44) | 3.25 (2.00-5.30) |

TABLE 6

| Type of event | Optimal PCT cut-off concentration [ng/mL] | Area under the receiver operator characteristics curve (AUC ROC) |
|---|---|---|
| Cardiac events | 0.0155 | 0.634 |
| Cerebrovascular events | 0.0215 | 0.628 |
| Cardiovascular mortality | 0.0215 | 0.640 |
| Total cardiovascular events | 0.0155 | 0.635 |
| Cancer mortality | 0.0155 | 0.585 |
| Total mortality | 0.0205 | 0.610 |
| Diabetes | 0.0185 | 0.627 |

TABLE 7

| | Q1 | Q2 | Q3 | Q4 | Q5 | |
|---|---|---|---|---|---|---|
| No. of subjects | 1045 | 1069 | 958 | 1214 | 1006 | |
| Procalcitonin Range [ng/mL] | 0.007-0.012 | 0.013-0.014 | 0.015-0.016 | 0.017-0.020 | 0.021-0.098 | |
| Total mortality | | | | | | |
| No. of cases (%) | 12 (1.1) | 28 (2.6) | 23 (2.4) | 34 (2.8) | 49 (4.9) | <0.001 |
| Hazard Ratio (95% CI) | 1.0 | 2.32 (1.18-4.57) | 2.12 (1.06-4.27) | 2.47 (1.28-4.78) | 4.35 (2.32-8.19) | |
| Total cardiovascular mortality | | | | | | |
| No. of cases (%) | 1 (0.1) | 5 (0.5) | 7 (0.7) | 6 (0.5) | 11 (1.1) | 0.007 |
| Hazard Ratio (95% CI) | 1.0 | 4.98 (0.58-42.62) | 7.76 (0.95-63.11) | 5.25 (0.63-43.58) | 11.75 (1.52-91.04) | |
| Cancer mortality | | | | | | |
| No. of cases (%) | 11 (1.1) | 15 (1.4) | 14 (1.5) | 23 (1.9) | 26 (2.6) | 0.004 |
| Hazard Ratio (95% CI) | 1.0 | 1.36 (0.62-2.96) | 1.41 (0.64-3.11) | 1.83 (0.89-3.75) | 2.52 (1.25-5.11) | |
| Cardiac events | | | | | | |
| No. of cases (%) | 8 (0.8) | 12 (1.1) | 20 (2.1) | 24 (2.0) | 34 (3.4) | <0.001 |
| Hazard Ratio (95% CI) | 1.0 | 1.50 (0.61-3.68) | 2.79 (1.23-6.34) | 2.65 (1.19-5.90) | 4.60 (2.13-9.93) | |

TABLE 7-continued

| | Q1 | Q2 | Q3 | Q4 | Q5 | |
|---|---|---|---|---|---|---|
| Cerebrovascular events | | | | | | |
| No. of cases (%) | 6 (0.6) | 10 (0.9) | 8 (0.8) | 14 (1.2) | 23 (2.3) | 0.001 |
| Hazard Ratio | 1.0 | 1.66 | 1.48 | 2.05 | 4.13 | |
| (95% CI) | | (0.60-4.57) | (0.51-4.27) | (0.79-5.32) | (1.68-10.15) | |
| Total cardiovascular events | | | | | | |
| No. of cases (%) | 13 (1.2) | 25 (2.3) | 33 (3.4) | 40 (3.3) | 61 (6.1) | <0.001 |
| Hazard Ratio | 1.0 | 1.93 | 2.83 | 2.72 | 5.10 | |
| (95% CI) | | (0.98-3.76) | (1.49-5.38) | (1.45-5.08) | (2.80-9.29) | |
| No. of persons | 845 | 834 | 745 | 978 | 791 | |
| Procalcitonin Range [ng/mL] | 0.007-0.012 | 0.013-0.014 | 0.015-0.016 | 0.017-0.020 | 0.021-0.096 | |
| Diabetes | | | | | | |
| No. of cases (%) | 13 (1.5) | 16 (1.9) | 21 (2.8) | 27 (2.8) | 44 (5.6) | <0.001 |
| Odds Ratio | 1.0 | 1.25 | 1.86 | 1.82 | 3.77 | |
| (95% CI) | | (0.60-2.62) | (0.92-3.73) | (0.93-3.54) | (2.01-7.05) | |

Sequence

```
SEQ ID NO: 1 (amino acid sequence of PCT):
  1 APFRSALESS PADPATLSED EARLLLAALV QDYVQMKASE LEQEQEREGS

51 SLDSPRSKRC GNLSTCMLGT YTQDFNKFHT FPQTAIGVGA PGKKRDMSSD

101 LERDHRPHVS MPQNAN
```

The invention claimed is:

1. A method comprising:
preparing a sample comprising bodily fluid from a subject wherein said bodily fluid is selected from the group consisting of blood, serum and plasma from the subject and
a capture molecule which binds to amino acids 2 to 116 or 3 to 116 of the amino acid sequence of SEQ ID NO. 1,
wherein a level of procalcitonin (PCT) in the sample is at least 0.0155 ng/ml, and wherein the subject is an apparently healthy adult human wherein apparently healthy is defined as the subject being free of symptomatic infections; having baseline level of PCT which is no greater than 0.25 ng/ml; and wherein the subject has not had surgery or experienced physical trauma within 7 days prior to measuring the baseline level of PCT.

2. The method of claim 1, wherein the level of PCT in the sample is at least 0.0185 ng/ml.

3. The method of claim 1, wherein the level of PCT in the sample is at least 0.0205 ng/ml.

4. The method of claim 1 wherein the level of PCT in the sample is at least 0.0215 ng/ml.

* * * * *

```
                          SEQUENCE LISTING

<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115
```